United States Patent [19]

Douglas

[11] Patent Number: 4,847,510

[45] Date of Patent: Jul. 11, 1989

[54] METHOD FOR COMPARISON OF SURFACES

[75] Inventor: Paul I. Douglas, The Woodlands, Tex.

[73] Assignee: Shell Oil Company, Houston, Tex.

[21] Appl. No.: 130,508

[22] Filed: Dec. 9, 1987

[51] Int. Cl.$^4$ ............................................. G01N 21/86
[52] U.S. Cl. .................................... 250/560; 250/561; 356/371; 356/394
[58] Field of Search ............... 356/371, 376, 394, 392; 250/561, 562, 563, 572, 571, 560; 364/562, 563; 382/8, 30; 358/107, 106

[56] References Cited

U.S. PATENT DOCUMENTS

| | | | |
|---|---|---|---|
| 4,290,698 | 9/1981 | Milana | 356/371 |
| 4,561,103 | 12/1985 | Horiguchi et al. | 356/394 |
| 4,641,357 | 2/1987 | Satoh | 250/561 |
| 4,650,334 | 3/1987 | Alster et al. | 356/394 |
| 4,677,680 | 6/1987 | Harima et al. | 356/394 |

Primary Examiner—David C. Nelms
Assistant Examiner—Michael Messinger
Attorney, Agent, or Firm—Paul I. Douglas

[57] ABSTRACT

A method is presented for the comparison of a second surface with a normalized surface model generated by reference to a group of esthetically acceptable first surfaces. A light pattern is typically projected onto a plurality of first surfaces moving beneath a light projection apparatus such that the light reflected from the first surfaces is received by a light receiver apparatus, and thereafter evaluated by appropriate computer software to define a nominal surface for the first group of esthetically acceptable surfaces. Each additional second surface passed below the light projection and light receiver apparatus is then compared to the normalized model generated by the first articles, such that undesirable surface deformities in the second article become readily apparent.

5 Claims, 2 Drawing Sheets

METHOD FOR COMPARISON OF SURFACES

RELATED APPLICATION

This application is related to an application entitled "Method and Apparatus for Detection of Undesirable Surface Deformities", Serial No. 050,435, filed May 18, 1987, inventors Mssrs. John D. Jobe and Mr. Allen E. Lepley.

BACKGROUND OF THE INVENTION

It has always been desirable to compare one acceptable surface of one article, (or a collection of acceptable surfaces of a collection of articles), with a second surface of a second article so as to detect and correct the cause of any undesirable surface deformities that may exist in the second surface.

For example, in the case of the outer surface of an automobile, any visible surface deformities, such as waviness in the surface, or "orange peel" in the paint surface, that can be eliminated enhance the esthetic and therefore the commercial value of the entire automobile. The competitive need to eliminate undesirable surface deformities in an automobile's outer surface becomes particularly important in the case of exterior automobile panels fabricated from fiber reinforced plastics, i.e., fiberglass components, wherein the panel may already have a certain degree of waviness due to the fiberglass mold conditions, resin cure rates, or other conditions of the fabrication process that tend to generate a surface waviness.

One surface deformity measurement system has been developed by the Budd Company, Plastic Research and Development Center, Troy, Mich. The Budd system moves a height gauge across the surface to be studied in order to attempt to measure the minute dimensions of surface deformities. This system is highly susceptible to background vibrations, can only measure one linear foot at a time, and is impractically slow in analyzing a large area. The system, due to these and other mechanical limitations, has not been placed in extensive use.

Another Diffracto Sight system, offered for sale by Diffracto, Inc., P. O. Box 36716, Grosse Point Woods, Detroit, Mich. 48236, is also available wherein light is reflected off the surface of interest, the light then being viewed through special lens worn by the viewer. The system merely yields a visual representation of any surface deformities, with no means of reducing the viewed image of the distorted surface into any type of objective format for further study.

A system need be developed, therefore, that presents any undesirable deformities in a surface in a readily visible format, the system also being capable of reducing the observed deformities into an objective format for further analysis. Such a system should identify the location of any unacceptable surface deformities, and also perform an objective and quantitative analysis as to the extent and magnitude of these deformities.

SUMMARY OF THE INVENTION

In a preferred embodiment of the present invention, a group of first articles which have acceptable surface finishes are placed on an assembly line and thereafter passed beneath a light pattern source and light pattern receiver, the light pattern receiver being coupled to an appropriate computer capable of defining a "nominal" acceptable surface after receipt of the light reflected from the surfaces of the first articles. The nominal surface is thereafter used as a reference against which future articles are compared.

Since the determination of whether a surface is acceptable is primarily as esthetic consideration, fabrication personnel or quality control supervisors may be used to select the first group of articles to be used to define the nominal reference surface.

Once the nominal surface has been defined, a second article having unknown surface qualities is placed on the assembly line and, by use of the light pattern source, light pattern receiver and computer, is compared to the nominal surface. If the second article's surface exceeds by an unacceptable amount the shape of the nominal surface, the second article will be rejected. In this manner the process used to fabricate the articles will be monitored to ensure that the process conditions used to produce the acceptable surface finishes do not vary from a standardized norm.

It is therefore an object of the invention to quantify the amount of the undesirable surface deformities that may exist in a second article when compared against a first group of articles having acceptable surfaces.

It is a further object of the present invention to describe a commercially viable surface deformity measurement system.

It is a further object of the invention, after the deformities in a particular surface have been quantified, to compare the quantitative measurement of the deformities in one surface to the quantitative measurement of deformities in another surface, so as to select one manufactured part above another for commercial use and sale.

It is a feature of the present invention to generate a known light pattern from a light pattern source, reflect the light pattern from the surface of interest, receive the reflected light pattern by a light pattern receiver such as a camera, and, by the use of a computer with appropriate software, convert the reflected light pattern into at least one defined edge that may be averaged with other defined edges from acceptable surfaces so as to generate a nominal surface.

It is a further feature of the present invention to generate other defined edges from a second article, and to thereafter compare these edges with the edges that define the nominal surface, so as to quantify the amount of undesirable surface deformities that may exist in the second surface.

These and other features, objects and advantages of the present invention will become apparent from the following detailed description, wherein references are made to the Figures in the accompanying drawings.

DESCRIPTION OF THE PREFERRED EMBODIMENT

Figure 1:
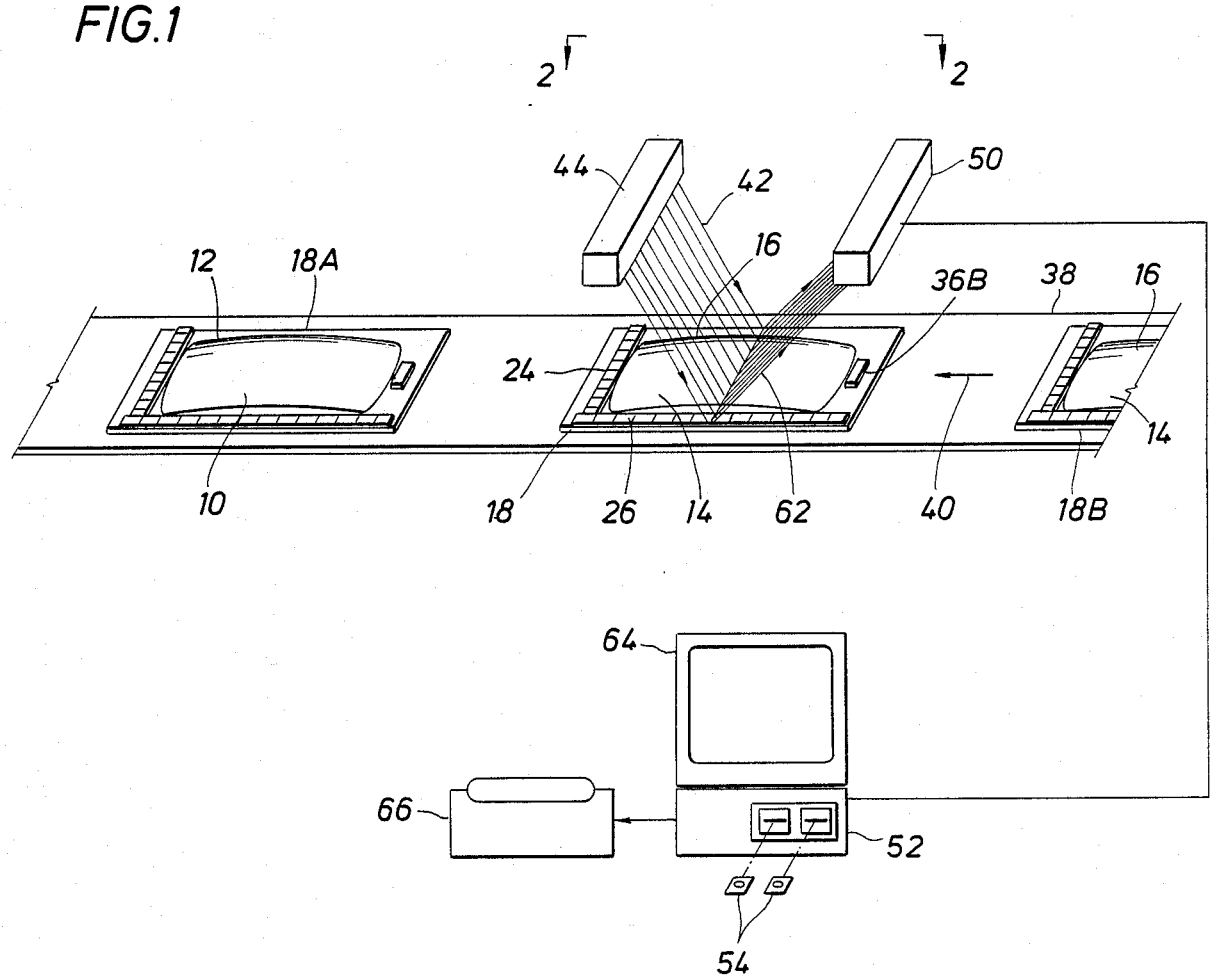
FIG. 1 is an isometric view showing articles carried by an assembly line beneath a light pattern source and light pattern receiver.

Referring now to FIGS. 1–5 a method of comparing the first surfaces 10 of a plurality of first articles 12 with a second surface 14 of a second article 16 may now be explained in further detail.

The article carriers 18, 18A, 18B typically carry all of the articles used in the comparison process, and have index location mirrors 20 (FIG. 2) positioned adjacent the carried location of either the first articles 12 or the second article 16. As explained later, the index mirrors 20 are located outside the periphery of the articles 12, 16 so as to define edge locus positions 22 relative to the surfaces of the carried articles.

Index location mirrors 20 are incorporated in a spaced manner on X axis index shoulder 24 and Y axis index shoulder 26 so as to define respectively the X axis index locations 28 and Y axis index locations 30. In the discussion that follows, the X7 index location 32 and Y7 index location 34 will also be referred to as the first index location and second index location respectively.

Inspection of the article carriers 18, 18A, 18B shows the index shoulders 24, 26 along with shoulders 36A, 36B cause the articles to remain fixed relative to the index locations 28, 30 respectively as the articles are carried down the assembly line 38 in the direction of motion indicated by arrow 40.

As can be seen in FIG. 1, article carrier 18A has already caused first article 12 to move beneath a light pattern 42 projected from a light pattern source 44. Such light pattern source 44 may have fluorescent light tubes carried by a support frame as is well known to the art. It should be well recognized that many other light pattern sources may be used that would project a light pattern having a discernible edge upon surfaces 10, 14.

The light pattern 42 projected on the surface 14 of second article 16 causes the surface to be visually divided into a light area 46 and a dark area 48 depending of course on the spread of the projected light pattern 42 upon the surface 14. To enhance the contrast between areas 46, 48 the surface 14 may be coated with a highlighting oil or other suitable liquid which would increase the amount of light reflected from the surface(s) 10, 14.

In the method of the present invention, as the article carrier and first article(s) 12 are moved beneath the light pattern 42 the projected light pattern 42 is reflected from the index mirrors 20 and the first surfaces 10 of the first article(s) 12 and is thereafter received at the light pattern receiver 50 as a first surface reflected light pattern.

Additional first articles 12 are selected from the production run and carried beneath the light source and light pattern receiver, the first articles being selected for their esthetically pleasing surface finishes.

The first surface reflected light patterns from the series of first articles 12 is then converted by the computer 52 and its incorporated software 54 into at least one surface array 56 (FIG. 3) of pixels 58 having values representative of the pixel value axis 60. Each pixel 58 value is representative of the intensity of light received from a portion of the first surface reflected light pattern.

The light pattern receiver 50 comprises in a preferred embodiment a camera located in the path of the reflected light pattern 62 and oriented as is well known to the art.so as to optically receive the reflected light pattern 62. The camera forming the light pattern receiver 50 in a preferred embodiment comprises a DAGE-MPI CC-68 instrumentation camera manufactured by DAGE-MPI, Inc. of Michigan City, Ind., having a 1,025/60 line resolution with a 2:1 linear scan and equipped with a zoom lens.

It should be well recognized that other cameras well known to the art may also be used to accomplish the teachings of the present invention.

The computer 52 comprises in a preferred embodiment an IBM PC-18 Model, having a Sony model GDM-1901-12 Model CRT display 64 and a Honeywell VGR-5000 printer 66, Model No. VGR-5H5HODGTO as peripheral equipment. The software 54 comprises in a preferred embodiment an "Image Pro" software package with "Doctor Halo" graphic software, used in combination with "PC-eye" video capture software, the PC-eye software available for purchase from Coors Data Systems, Merrimack, N.H., the Image Pro software available from Media Sybernetics, Inc.

The software 54 may be modified from its purchased format in order to accomplish the desired teachings of the present invention, by those having ordinary skill in the art.

Returning to the general discussion, a plurality of the first surface arrays are then evaluated to define a series of nominal edge(s) 68. For the purpose of clarity only one nominal edge 68 at position Y7 is shown, though it should be understood that a nominal edge is defined for each Y-axis index location Y1–Y13. It should be noted that the index location mirrors 20 are separated on the index shoulders 26, 24 by non-reflective surface areas 70 so as to provide a clear distinction of the exact location of the index locations 28, 30 relative to the reference axis 72 (FIG. 2).

Figure 2:
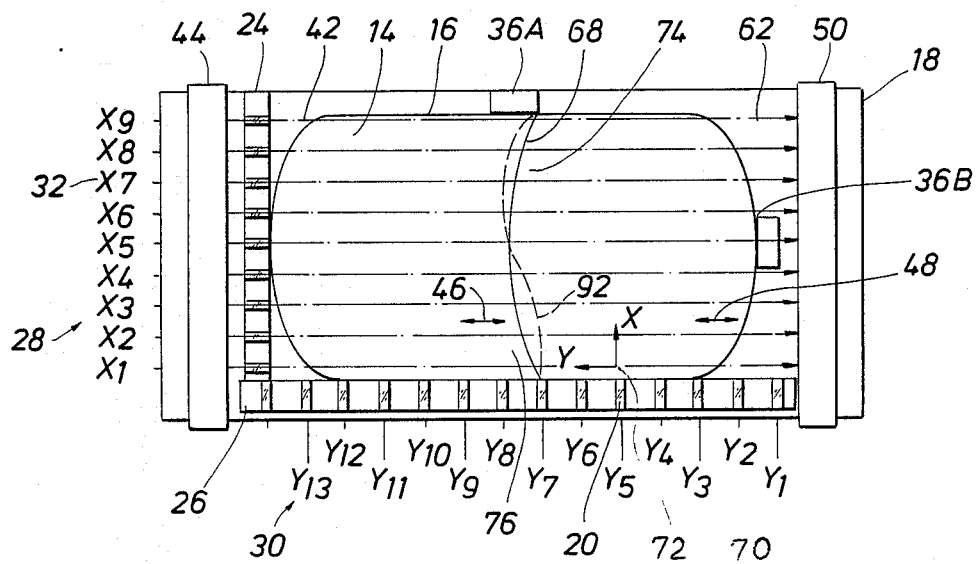
FIG. 2 shows a schematic representation in a plan view taken along lines 2—2 of FIG. 1 of a second article carried by an article carrier.

It should be noted in review of FIG. 2 that the particular surface 14 can be seen to have a high area surface deformity 74 as well as a low area surface deformity 76, which causes the second surface defined edge 92 to curl away from the nominal edge 68 at these deformities.

Figure 3:
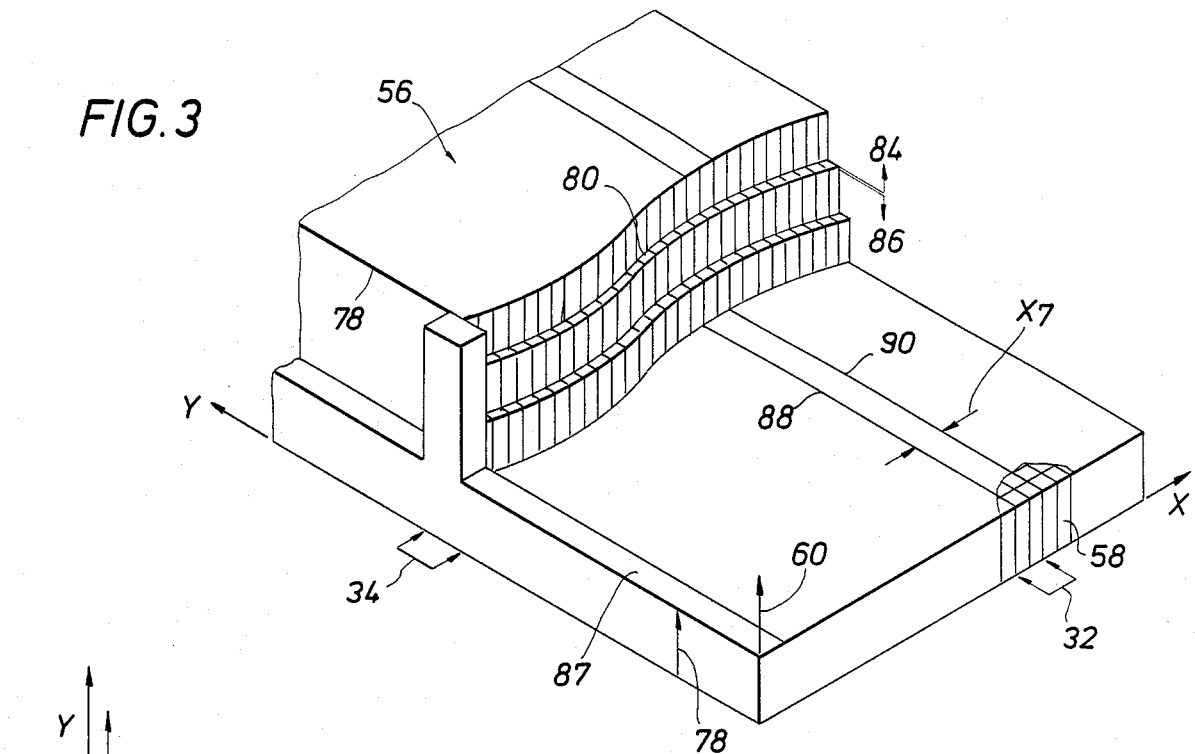
FIG. 3 is pictorial representation showing a pixel array comprised of individual pixels, the value of each pixel plotted relative to a pixel value axis.
Figure 4:
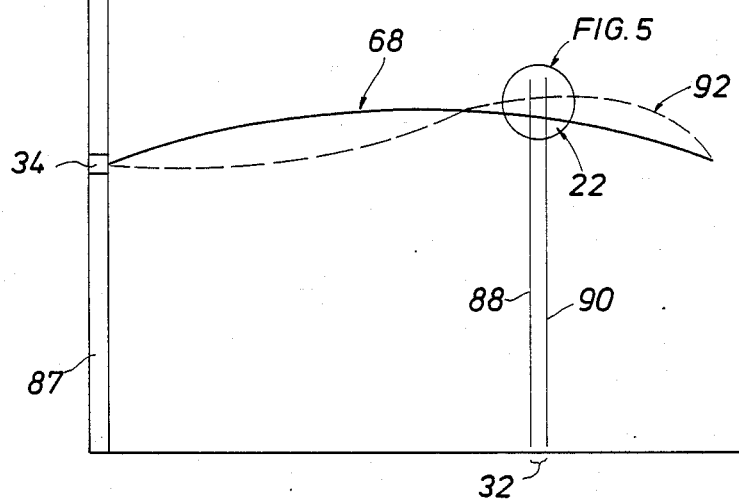
FIG. 4 is a graphical representation showing a first surface nominal edge and second surface defined edge for an X7, Y7 edge locus position.
Figure 5:
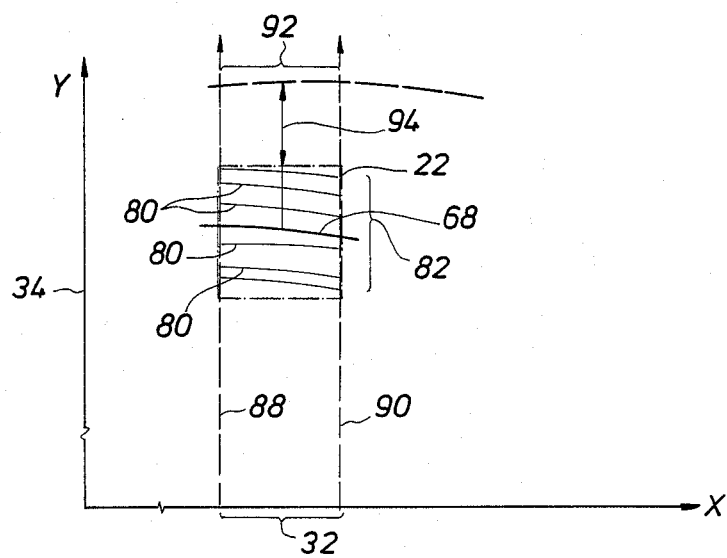
FIG. 5 is a graphical representation taken from within the circle on FIG. 4 labeled "FIG. 5" showing the position of a second surface defined edge realtive to the position of a first surface nominal edge at edge locus position X7, Y7.

Referring now to FIGS. 3, 4 and 5, the first surface reflected light patterns that have been converted into differing pixel values of the first surface array as the first article(s) move beneath the light pattern receiver are thereafter evaluated at predetermined increments of motion to define the nominal edge(s) 68, as follows. First, both the dark area pixel values 78 and light area pixel values 78A of each first surface array 56 are evaluated at each Y-axis index location 30 as the light reflects off each Y-axis index location mirror 20, by the software 54 in order to define an edge 80 for each respective Y-axis index location. The motion of the first article beneath the light pattern receiver is effectively "frozen" at each Y-axis index location and the value of each pixel recorded.

Each first article therefore generates one separate defined edge 80 at each separate index location Y1–Y13.

FIG. 5 shows all of the defined edges 80 of the all of the first surfaces at location X7, Y7. The X7 index location has been defined by the index location mirror 20 on th X-axis indexed shoulder 24 at position X7. The index mirrors are therefore used to generate a standardized coordinate "grid" across the surface of each of the articles. The spacing of the mirrors from one another, as well as the width of the mirrors, may be adjusted as desired to effect the overall sensitivity of the system to the detection of surface deformities.

The defined edges 80 for each first article at position X7, Y7 are shown in FIG. 5 positioned within the edge locus position 22. The position of the entire collection of defined edges 80 within edge locus position 22 are then averaged to arrive at a first surface nominal edge 68. All of the nominal edges 68 for all of the Y-axis index locations define the nominal surface mentioned earlier.

Returning now to FIG. 3, evaluation of the pixel values 78, 78A of each first surface array 56 to define the edge 80 for each respective first surface reflected light pattern at a particular Y-axis index location may be done by the following steps. The first surface array 56 first surface pixels having a selected value as well as first surface pixels having a value greater than the selected value are segregated into a first group 84. The first surface pixels having less than the selected value are segregated into a second group 86 by the computer software. An edge 80 of the first surface reflected light pattern may thereafter be defined at the boundary of the first group 84 of first surface pixels and the second group 86 of first surface pixels.

It should be noted that the same method is used to evaluate the value of the second surface pixels in order to define at least one edge 92 of the second surface reflected light pattern.

The step of averaging the positions of the defined edges 80 to define a nominal edge 68 may be explained as follows. For example, for position XY, Y7 the edge locus position 22 is defined at the intersection of the defined edges 80 between line A 88 and line B 90. These lines 88, 90 are oriented substantially perpendicular to the defined edges 80 and pass through a first index location 32 which has been generated by the X7 location index location mirror 20. The defined edges 80 intersect these lines 88, 90 when one end of each defined edge 80 coincides with a Y7 second index location 34.

It should be noted that each defined edge 80 is therefore "fixed" at its intersection with the Y-axis, while the remainder of the edge 80 defines edge locus positions 22 at each intersection of the edge 80 with line(s) passing through each X-axis index location. Fixation of one end of each edge 80 insures that a standardized comparison process may be conducted between all of the articles 12, 16.

The positions of the defined edges 80 located within the edge locus position(s) 22 indicate a locus of lines of acceptable surface variations.

In a preferred embodiment of the present invention, all of the defined edges within all of the edge locus positions are thereafter averaged relative to the distance of the defined edges away from their respective first index location(s) 32. In this manner, the location of each defined edge 80 within each edge locus position is weighed such that the nominal location of all of the defined edges within each edge locus position 22 is thereafter defined as the first surface nominal edge 68.

It should be well recognized that a mathematical line generation function may be used to connect the nominal edges of each edge locus position into a common line relative to each Y-axis index location if it is desired. Since the comparison process, however, between the first article(s) surface(s) and the second article, is only conducted at each edge locus position, this is not necessary in the preferred embodiment of the present invention.

As can be seen in FIG. 2 the first surface nominal edge 68 represents the location of an acceptable surface reflection from a nominal surface. Nominal edge 68 thereby represents the preferred esthetically acceptable location of the point of reflection of the projected light pattern 42 from the surface of an acceptable article prior to receipt of the light pattern by the light pattern receiver 50. The first surfaces have been selected after esthetic comparison with other surfaces. No extensive mathematical calculations are necessary to define an ideal first surface by the method of the present invention, since the "acceptability" of any surface is only an esthetic, not mathematical, consideration.

Once a nominal edge 68 has been defined for each Y axis index location 30 by selection of a proper number of first articles 12, second articles 16 may be thereafter placed on the article carrier. It should be well understood, of course, that if it is desired to use only a singular first article 12 as a reference, the above steps may be utilized to conclude with a definition of a first surface nominal edge 68 after reference to only one first surface.

The second article is moved in a similar manner beneath the same light pattern 42 projected from the light pattern source 44. It should be well recognized that other light pattern projection mechanisms and light pattern receiver mechanisms may be used to accomplish the same mechanical result.

A second surface reflected light pattern is similarly received by the light pattern receiver 50 wherein the reflected light pattern has been reflected from the index mirrors 20 and the surface 14 of the second article 16. The second surface reflected light pattern is thereafter converted in a similar manner as was done with the first surface(s) into a second surface array of pixel values, (such as shown in FIG. 3), and wherein thereafter the value of the second surface pixels are evaluated to define at least one edge 92 of the second surface reflected light pattern. It should be noted that the second surface defined edge 92 is properly indexed to the first surface nominal edge 68, for example, at location X7, Y7 by use of the same Y axis and X axis index locations 30, 28 respectively incorporated within the X axis index shoulder 24 and Y axis index shoulder 26. These shoulders 24, 26 properly position the second article in the same position on the article carrier as the first article 12 was originally carried.

The nominal edge 68 is then compared with the edge 92 of the second surface reflected light pattern, (as shown in FIG. 5). As can be seen at position X7, Y7 a deviation from the nominal edge 68 exists due to the presence of the high area surface deformities 74 (FIG. 2). The amount of deviation of defined edge 92 away from nominal edge 68 may be readily measured by comparison of the coordinates of the pixels representing each edge 68, 92. An accept/reject decision may then be made for the second article, dependent on the amount of measured deviation.

It may be decided, for example, that if the the second surface defined edge 92 is outside the edge locus position 22 then the second article should be rejected. In a like manner, all of the second surface defined edges generated at all of the edge locus positions may be analyzed to determine if the second article exhibits any undesirable surface deviations due to high or low area surface deformities.

It should be apparent from viewing FIG. 5 that the X7 index location 32 width through the surface array may be established by the width of the X7 index location mirror. It should also be recognized that in a preferred embodiment, a Y index location track 87, (FIGS. 3 & 4), may be designated within an edge portion of the surface array so as to cause the proper alignment of the reflected light patterns edges 80, 82, 92 with their respective Y7 index location 34. The occurrence in the location track 87 of light area pixel values indicates the reception of light from a Y-axis index location mirror 20. This pixel value "peak" is used to indicate the location in the array of one end of defined edges 80, 92, and the location of one end of the nominal edge 68.

Many other variations and modifications may be made in the apparatus and techniques herein before described by those having experience in this technology without departing from the concept of the present invention. Accordingly, it should be clearly understood that the apparatus and methods depicted in the accompanying drawings and referred to in the foregoing description are illustrative only and are not intended as limitations on the scope of the invention.

I claim as my invention:

1. A method of comparing the first surfaces of a plurality of first articles with a second surface of a second article, said method comprising the following steps:
   providing at least one article carrier having index location mirrors positioned adjacent the carried location of said article on said article carrier, said index location mirrors located so as to define edge locus positions relative to the surface of said article;
   placing at least one of said first articles on said at least one article carrier;
   moving said article carriers and said first articles beneath a light pattern projected from a light pattern source;
   receiving at a light pattern receiver at least one first surface reflected light pattern reflected from said index location mirrors and said at least one first surface of said at least one first article;
   converting said at least one first surface reflected light pattern into at least one first surface array of pixel values, each pixel value representing the intensity of light received from a portion of said at least one first surface reflected light pattern;
   evaluating a plurality of said first surface arrays to define a nominal edge;
   placing a second article on said article carrier;
   moving said article carrier and said second article beneath a light pattern projected from said light pattern source;
   receiving at said light pattern receiver a second surface reflected light pattern reflected from said index location mirrors and said at least one second surface;
   converting said second surface reflected light pattern into a second surface array of pixel values, each pixel value representing the intensity of light received from a portion of the second surface reflected light pattern;
   evaluating the value of said second surface pixels to define at least one edge of said second surface reflected light pattern; and
   comparing said nominal edge of said first surfaces with said at least one edge of said second surface reflected light pattern.

2. The method of claim 1, wherein the step of evaluating the pixel values within a plurality of said first surface arrays to define a nominal edge, is done by:
   evaluating the pixel values of each first surface array to define an edge for each respective first surface reflected light pattern; and
   averaging the position of said defined edges to define said nominal edge.

3. The method of claim 2 wherein the step of evaluating the pixel values of each first surface array to define an edge for each respective first surface reflected light pattern is done by:
   segregating for each first surface array first surface pixels having a selected value greater than said selected value into a first group;
   segregating for each first surface array first surface pixels having less than said selected value into a second group; and
   defining an edge of said first surface reflected light pattern at the boundary of said first group of first surface pixels and said second group of first surface pixels.

4. The method of claim 2 wherein the step of averaging the position of said defined edges of said first surface reflected light patterns to define said nominal edge is done by:
   defining said edge locus position on said first surface array at the intersection of said defined edges with at least one line oriented substantially perpendicular to said defined edges and passing through a first index location generated in said first surface array by receipt of light reflected from one of said index location mirrors, when one end of said defined edges coincides with a second index location generated in said first surface array by receipt of light reflected from another of said index location mirrors;
   averaging the position of said defined edges within said edge locus position relative to the distances of the defined edges away from said first index location; and
   defining the average position of the defined edges within said edge locus position as the normal edge.

5. The method of claim 1 wherein the step of evaluating the value of said second surface pixels to define at least one edge of said second surface reflected light pattern is done by:
   segregating second surface pixels having a selected value and second surface pixels having a value greater than said selected value into a first group;
   segregating second surface pixels having less than said selected value into a second group; and
   defining at least one edge of said second surface reflected light pattern at the boundary of said first group and said second group of second surface pixels.

* * * * *